United States Patent
Fritze et al.

(10) Patent No.: US 8,308,333 B2
(45) Date of Patent: Nov. 13, 2012

(54) SURGICAL LAMP WITH ILLUMINATED HANDLES

(75) Inventors: Dirk Fritze, Emmering (DE); Kamran Tahbazian, Groebenzell (DE); Rudolf Marka, Ismaning (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 331 days.

(21) Appl. No.: 12/487,081

(22) Filed: Jun. 18, 2009

(65) Prior Publication Data

US 2009/0316394 A1 Dec. 24, 2009

(30) Foreign Application Priority Data

Jun. 20, 2008 (EP) .................................... 08011295

(51) Int. Cl.
*F21V 1/00* (2006.01)
(52) U.S. Cl. ..................... 362/572; 362/399; 362/311.02
(58) Field of Classification Search .................. 362/572, 362/573, 804, 33, 20, 276, 234, 311.01–311.03, 362/253, 399, 249.02–249.06; 600/249; 606/2, 10, 12; 16/110.1–114.1, 405–430; 433/29–31
See application file for complete search history.

(56) References Cited

U.S. PATENT DOCUMENTS

| | | | | |
|---|---|---|---|---|
| 4,605,124 A | * | 8/1986 | Sandel et al. | 362/399 |
| 5,023,515 A | * | 6/1991 | Olon et al. | 315/88 |
| 5,142,736 A | * | 9/1992 | Kuehn et al. | 362/804 |
| 6,739,744 B2 | * | 5/2004 | Williams et al. | 362/552 |
| 7,207,694 B1 | * | 4/2007 | Petrick | 362/240 |
| 7,311,410 B2 | * | 12/2007 | Marka | 362/33 |
| 7,450,028 B2 | * | 11/2008 | De Godzinsky | 340/815.45 |
| 2003/0014834 A1 | | 1/2003 | Naughton | |
| 2003/0210559 A1 | | 11/2003 | Jesurun et al. | |
| 2005/0195601 A1 | * | 9/2005 | Marka | 362/242 |
| 2006/0002110 A1 | * | 1/2006 | Dowling et al. | 362/252 |
| 2006/0239005 A1 | * | 10/2006 | De Godzinsky | 362/276 |
| 2008/0304281 A1 | * | 12/2008 | Scholz | 362/572 |

FOREIGN PATENT DOCUMENTS

| | | |
|---|---|---|
| EP | 0667485 A1 | 8/1995 |
| EP | 1064495 B1 | 1/2001 |
| EP | 1568934 | 2/2004 |
| WO | 2007014769 | 2/2007 |
| WO | 2007082960 A1 | 7/2007 |

OTHER PUBLICATIONS

European Search Report from corresponding European Application No. EP 08011295, mailed Nov. 26, 2008, 5 pages.

* cited by examiner

*Primary Examiner* — Bao Q Truong
(74) *Attorney, Agent, or Firm* — Fish & Richardson P.C.

(57) ABSTRACT

A surgical lamp that includes a carrying system, a lamp body, and at least one handle having an illuminant. The handle is at least partially formed of a translucent material.

32 Claims, 4 Drawing Sheets

SURGICAL LAMP WITH ILLUMINATED HANDLES

CROSS REFERENCE TO RELATED APPLICATION

This application claims priority under 35 U.S.C. §119(a) to European Patent Application No. 08 011 295.6, filed Jun. 20, 2008, the entire contents of which are hereby incorporated by reference.

TECHNICAL FIELD

The invention relates to a surgical lamp with illuminated handles.

BACKGROUND

Surgical lamps are typically attached to the ceiling of an operating theatre, to a wall, or to a movable stand by means of a so called carrying system. Usually, the carrying system includes a first boom that is pivotable about a vertical axis, and a second boom that is horizontally pivotable and height-adjustable. With this carrying system, the surgical lamp can be positioned at any of various different locations in the room for illuminating a surgical site.

Usually, surgical lamps are provided with a handle that is located in a sterile area of the surgical lamp, and with which the sterile surgeon can position the surgical lamp.

Usually, surgical lamps are provided with additional handles at the outer circumference of the lamp body for positioning the lamp before surgery or during surgery, by non-sterile surgical personnel.

In recent years, surgical interventions using minimally invasive surgical techniques have increased. These surgeries are performed without large surgical openings but only with small openings through which optical equipment and surgical instruments are inserted. The view of the minimally invasive surgical site is shown by monitors that can be attached to the carrying system of the surgical lamp via a camera system.

When applying this technique, bright light of the surgical lamp is necessary at the beginning of the surgery when opening a part of a body for the surgery. During the minimally invasive surgery, the surgical lamp is switched off and the room illumination in the operating theatre is dimmed for improving the surgeon's view of the monitors, which display the view of the surgical site based on images transmitted from the endoscope.

SUMMARY

In one aspect of the invention, a surgical lamp includes a carrying system, a lamp body configured to emit light, at least one handle connected to the lamp body, and at least one illuminant disposed in the at least one handle. At least a portion of the handle has a translucent surface.

In some embodiments, the translucent surface of the handle is a structured surface such that light emitted by the at least one illuminant is diffusely emitted through the translucent surface.

In certain embodiments, the translucent surface of the handle is configured to allow light to pass therethrough in multiple different directions.

In some embodiments, the translucent surface includes at least first and second faces that abut one another.

In certain embodiments, the translucent surface has a curved shape.

In some embodiments, the translucent surface covers substantially the entire handle.

In certain embodiments, the handle is fixed to a surface of a housing of the lamp body.

In some embodiments, the translucent surface is configured so that it does not modify the color of light that is emitted by the at least one illuminant.

In certain embodiments, the translucent surface is configured to modify the color of light that is emitted by the at least one illuminant.

In some embodiments, the at least one illuminant is adapted to indicate a type of power supply being used to power the surgical lamp.

In certain embodiments, the surgical lamp is configured so that it can be operatively connected to a conventional power supply and to an auxiliary power supply, and the at least one illuminant is connected in such a way that operation with the auxiliary power supply is indicated.

In some embodiments, the emitted light has a different color when operating with the auxiliary power supply than when operating with the conventional power supply.

In certain embodiments, the surgical lamp can be supplied by a conventional power supply and by an auxiliary power supply, and the handle includes at least a second illuminant that indicates the operation with the auxiliary power supply.

In some embodiments, light emitted by the second illuminant has a different color than light emitted by the at least one illuminant.

In certain embodiments, a third illuminant is connected in such a way that a certain operating mode of the surgical lamp is indicated.

In some embodiments, a part of the translucent surface of the handle has a refractor-like construction.

In certain embodiments, light emitted through the part of the translucent surface having the refractor-like construction is emitted by at least a fourth illuminant.

In some embodiments, the fourth illuminant is configured to emit light within a narrow-band wavelength.

In another aspect of the invention, a method includes detecting a type of power supply being used to power a surgical lamp, and operating an illuminant of the surgical lamp to indicate the detected type of power supply to a user.

In some embodiments, the illuminant is located in a handle of the surgical lamp.

In some embodiments, the illuminant is operated in a manner to cause the illuminant to blink.

In some embodiments, the illuminant is operated to emit light of a first color if a first type of power supply is detected, and the illuminant is operated to emit light of a second color if a second type of power supply is detected.

According to a further aspect of the invention, a surgical lamp with a carrying system, a lamp body having a first light emission area and at least a handle having an illuminant is disclosed. The handle at least partially includes a translucent second light emission area (e.g., a translucent face).

By integrating illuminating elements into the handles, an easy and economic possibility is given for providing the surgical lamp with elements that emit light without being provided with additional elements. The light emitting area can be translucent, i.e., permeable for light without causing visibility of the light sources as with a transparent material.

In some embodiments, the translucent face includes a textured surface, i.e., a surface with an elevated pattern. The surface can, for example, be sandblasted or ribbed. In certain embodiments, the translucent face includes axially and circumferentially ribbed surfaces. Thereby, a surface having ball-shaped recesses, triangular elongated elevations, or pyramidal-shaped elevations is formed. The recesses or elevations are within a range of hundredths of millimeters. Thus, light is diffusely emitted out of the second light emitting surface such that it is not possible to identify the origin of the light, i.e., the illuminant.

In certain embodiments, the translucent face of the handle is constructed to allow light to be emitted through the translucent face in multiple different viewing directions. For example, the translucent face can include multiple surfaces that perpendicularly abut one another. Alternatively, the translucent face can include a curved surface. In certain embodiments, almost the entire housing of the handle includes the second light emitting surface.

In order to have good accessibility, the handle is typically attached to the outer circumference of the lamp body. However, in some embodiments, the handle is attached to the carrying system.

In certain embodiments, the color of the light emitted by the illuminant is not modified by the light emitting face. In some such embodiments, for example, light that is emitted by a white illuminant remains white after going through the light emitting face.

However, in other embodiments, the color of the emitted light is modified by the light emitting face. In some such embodiments, for example, white light that is emitted by the illuminant is modified by the light emitting face. The emitted white light can, for example, exit the emitting face as blue light.

In some embodiments, the illuminant is connected in such way that a power supply of the surgical lamp is indicated by the illuminant. For example, the illuminant can visually indicate at the surgical lamp whether the lamp was disconnected from the mains by the external main switch or whether the surgical lamp is in a standby-mode and can be directly switched on at the surgical lamp itself.

In the case of a supply of the surgical lamp with different power supplies, e.g., a conventional public power supply or a specific power supply having a battery-backed emergency power aggregate that immediately compensates a breakdown of the conventional public power supply, it is important to identify the kind of power supply being used. Thereby, the illuminant is connected in such a way that the illuminant shines during supply with the specific power supply to indicate that the specific power supply is being used. For example, the illuminant can shine or blink in a certain rhythm to indicate the type of power supply being used.

As an alternative to the shining or blinking of the illuminant, the color of the emitted light can be modified when a specific power supply is used. For example, in some embodiments, a color filter is positioned between the illuminant and the light emitting face by the external switch to the specific power supply.

In some embodiments, the operation with a specific power supply is indicated by at least a second specific illuminant in the handle. In such embodiments, the specific illuminant emits a different color than the illuminant, which indicates the operation with a specific power supply.

In certain embodiments, a third illuminant is connected in such a way that it indicates a specific operating status, e.g., the operation with a standardized distribution of the light intensity in the light field.

In some embodiments, a part of the second light emitting face has a refractor-like construction. Thereby, the light emitted from a fourth illuminant inside the handle is focused in such a way that when the illuminants in the first light emitting face of the lamp body are switched off, the surgical site for minimal invasive surgeries is illuminated. For achieving the aforementioned, the handle is provided with the fourth illuminant that emits light that is focused and emitted by the refractor.

For specific applications, such as, diagnostics, the light of the fourth illuminant has the characteristic that only oscillations in a narrow band of wavelength occur. In some embodiments, for example, an illumination having a wavelength of 450±5 nm is used in combination with fluorophor ("Fluorescein") that is injected in the tissue that is to be examined. The fluorophor is excited so that it irradiates. In this way, by using a filter which only allows light emitted by the fluorophor to pass therethrough, tissue identification can be performed.

The surgical lamps described herein can include elements that can easily and economically be illuminated, and that allow an easy identification of the position and the orientation of the surgical lamp.

Other aspects, features, and advantages are in the description, drawings, and claims.

DETAILED DESCRIPTION

Figure 1:
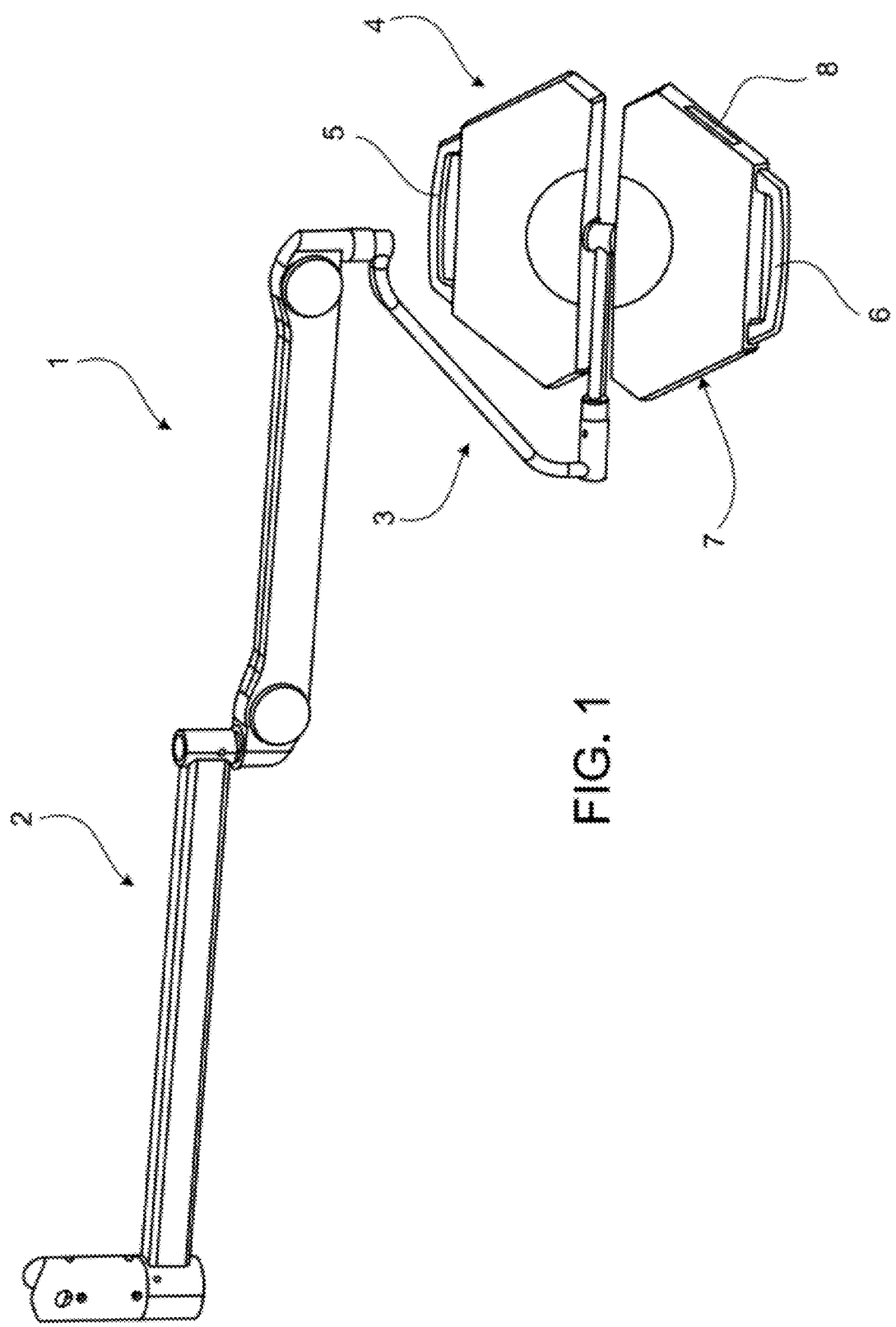
FIG. 1 is an isometric view of a surgical lamp.

FIG. 1 is an isometric view of a surgical lamp 1 that includes a carrying system 2, a suspension system 3, and a lamp body 4. The carrying system 2 is attached to a ceiling, a wall or a movable stand. By means of the carrying system 2 and the suspension system 3, the lamp body 4 is positionable in any arbitrary spatial position and orientation within a radius of action.

For non-sterile positioning of the lamp body 4, handles 5, 6 are attached to both halves of the lamp body 4. Both of the halves of the lamp body 4 are connected to one another in a torque-proof manner so that when pivoting one of the halves, the other half follows along in order to keep the light emitting faces in one plane.

A control device 7, which is described below, is arranged within the lamp body 4 in order to avoid the need for long cable connections. However, the control device 7 does not necessarily have to be in the lamp body 4. The control device 7 can, for example, be arranged in a discrete housing which is arranged at the lamp body 4 or at the suspension system 3 in order to make the lamp body 4 as small and streamlined as possible. Alternatively, the control device 7 can be located in an external operating unit located in a medical supply unit or in/at a wall.

An operating device 8 having switch elements and setting elements is arranged at the outside of the lamp body 4. However, the operating device 8 can alternatively be located in a discrete housing that is located, e.g., at the lamp body 4, at the suspension system 3, in a medical supply unit, or in/at a wall.

Figure 2:
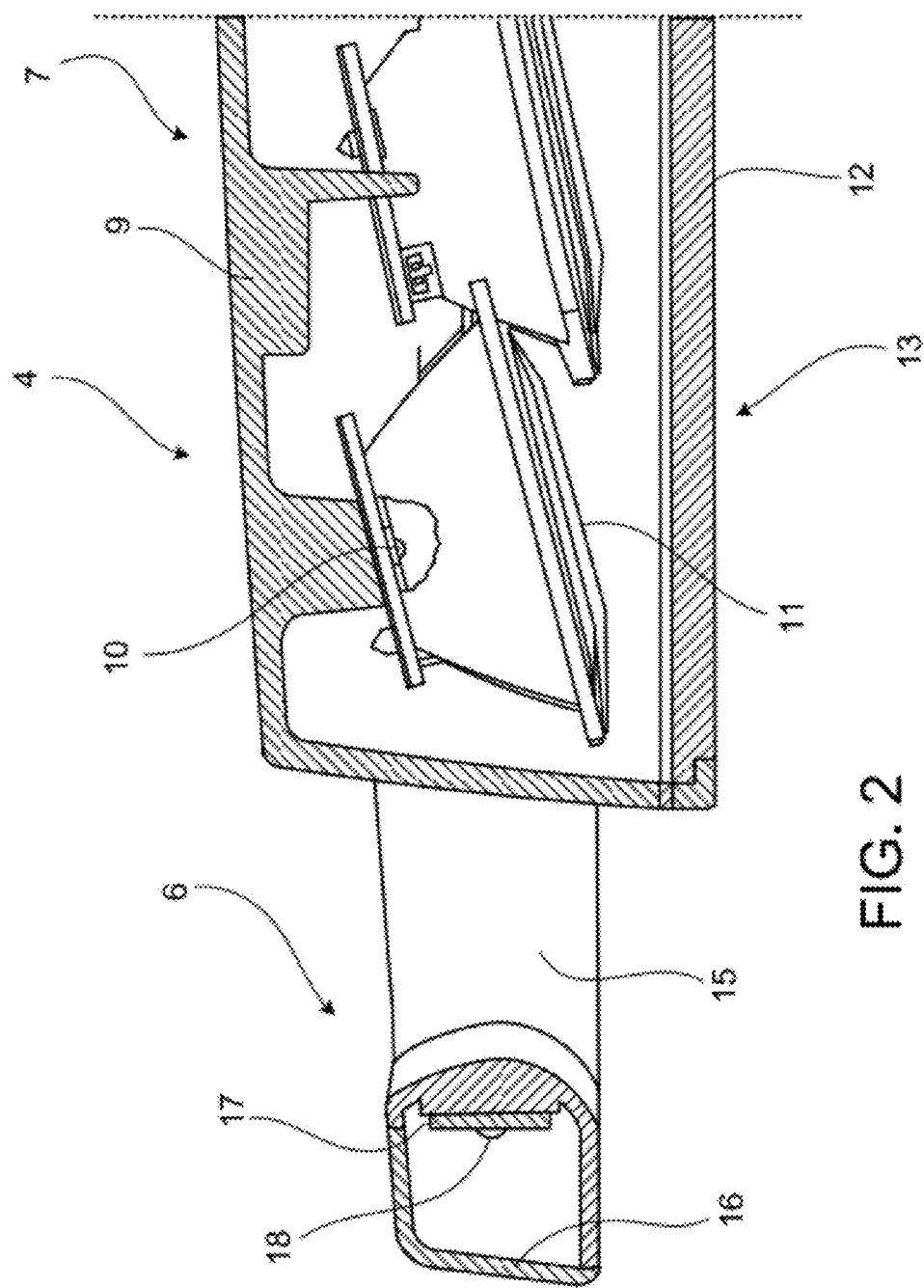
FIG. 2 a partial, sectional side view of a lamp body with a handle.

FIG. 2 shows a part of a sectional side view of the lamp body 4 and the handle 6. Inside a housing 9 of the lamp body 4, which is formed of aluminum die casting, illuminants 10 are attached to inclined attachment faces. The illuminants 10 irradiate bundled light beams via refractors 11 through a lower transparent cover plate 12, which is made of resin and forms a first light emitting face 13.

The cover plate 12 is attached to the housing 9. The light beams are directed to an operating field, which is located a certain distance from the lamp body 4. At the operating field, the light beams generate a light field, which is an area that is illuminated by the light beams.

The handle 6 includes two parts, an inner part 15 and an outer part 16. The inner part 15 is connected to the housing 9 by four screws. The outer part 16 is connected to the inner part 15 via a clip connection.

A circuit board stripe 17 is fixed to the inner part 15 by means of an adhesive tape. Ten illuminants 18, here LEDs, are fixed and electrically connected on the adhesive tape. Power is supplied to the circuit board stripe 17 by cables.

The control device 7 is located in the housing 9 of the lamp body 4. The control device 7 includes means for dimming and switching on and switching off the illuminants 10, such as current regulators, means for transmitting switching information and setting information of the switching elements and setting elements of the operating device 8, a storage area for storing operating parameters, and a CPU that calculates and determines the necessary adjustments for the means for dimming and switching on and switching off the illuminants 10 based on the stored operating parameters.

The control device 7 is connected to a power supply device, to the illuminants 18, to the illuminants 10, and to the operating device 8.

The operating device 8 (shown in FIG. 1) includes an element for switching the surgical lamp 1 on and off, an element for setting the distance between the lamp body 4 and the light fields 11, 11', 11", and an element for setting the brightness of the light fields 11, 11', 11".

In some embodiments, the operating device 8 is illuminated. It is optionally possible to illuminate the entire operating device, the displayed symbols, and the operating elements.

The element for switching the surgical lamp 1 on and off switches the surgical lamp 1 from a standby-mode in which the illuminants 10 do not shine to an operating mode and vice versa. In the operating mode, the illuminants 10 are operated according to the settings of the setting elements at the operating device 8. An external main switch is provided for completely switching the surgical lamp 1 off by disconnecting from the main power supply. When disconnecting the main power supply, the illuminants 18 are extinguished. Otherwise, the illuminants 18 shine in the standby-mode as well as in the operating mode of the surgical lamp 1.

Figure 3:
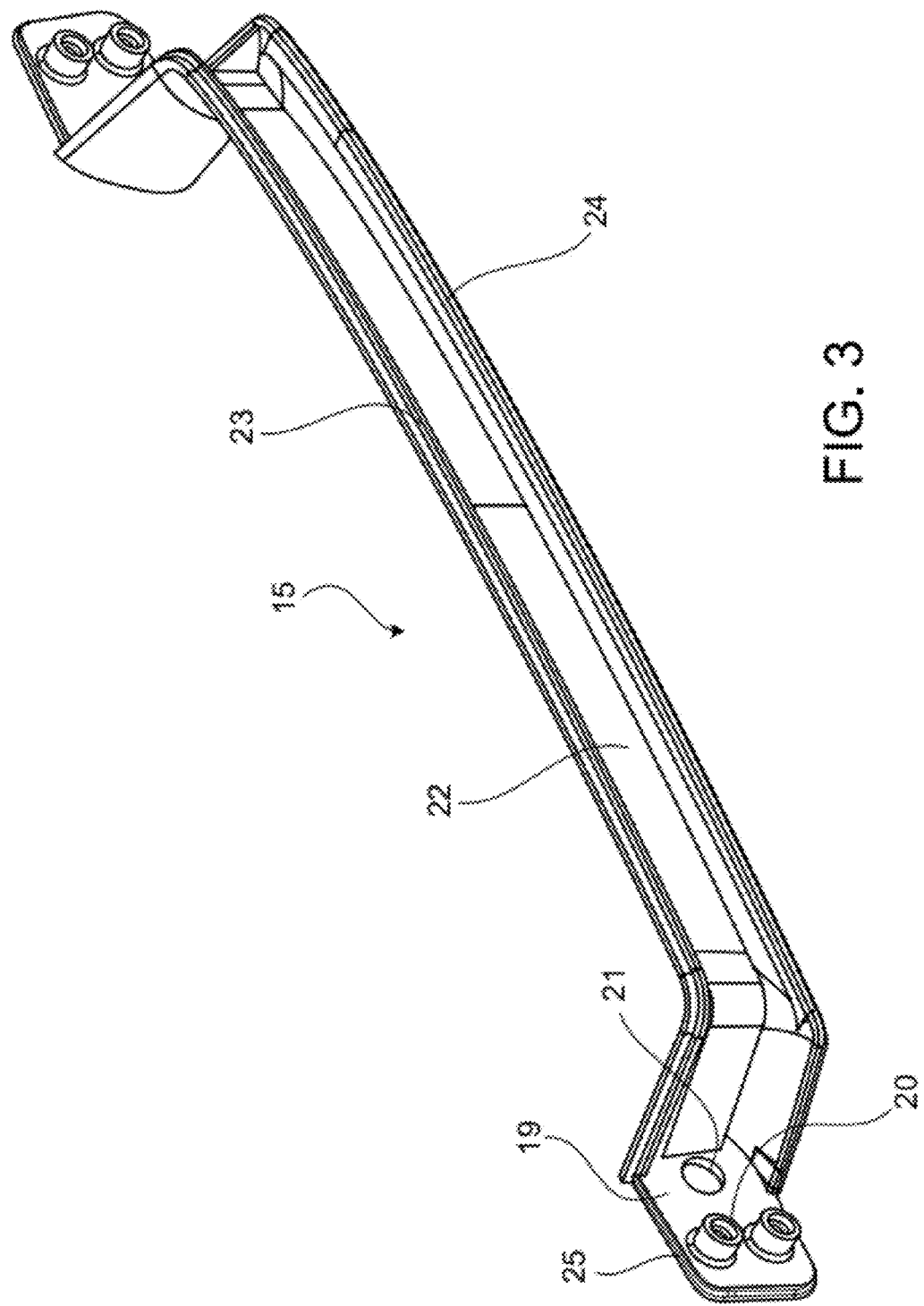
FIG. 3 is an isometric view of an inner part of the lamp body handle with an illuminant.

FIG. 3 shows an isometric view of the inner part 15 of the handle 6 with illuminants 18. It should be understood that the handle 5 is identical to the handle 6. To avoid redundancy, only the handle 6 is described in detail herein. The inner part 15 is ergonomically formed and it is provided with a screw-on bracket 19 at both of its ends. At these screw-on brackets 19, two domes 20 are provided for fixing the inner part 15 to the housing by means of two screws. Also at the screw-on brackets 19, a bore 21 is provided for leading through connecting cables between the control device 7 and the above mentioned circuit board stripe 17 into the housing 9.

On the inner side of the inner part 15, a bulge of material is provided in its longitudinal direction, which constitutes a fixing face 22 for the circuit board stripe 17. At the outer side of an upper and lower edge of the inner part 15, a part of the clip connection 23, 24 is circumferentially arranged from the fixing face 22 to the opposite fixing face. At both of the screw-on brackets 19, a part of a clip connection 25 is also arranged. The inner part 15 is made of a translucent plastic material via injection molding. By using translucent material, all of the faces that are visible from the outside, except the screw-on brackets, constitute the second light emitting area.

Figure 4:
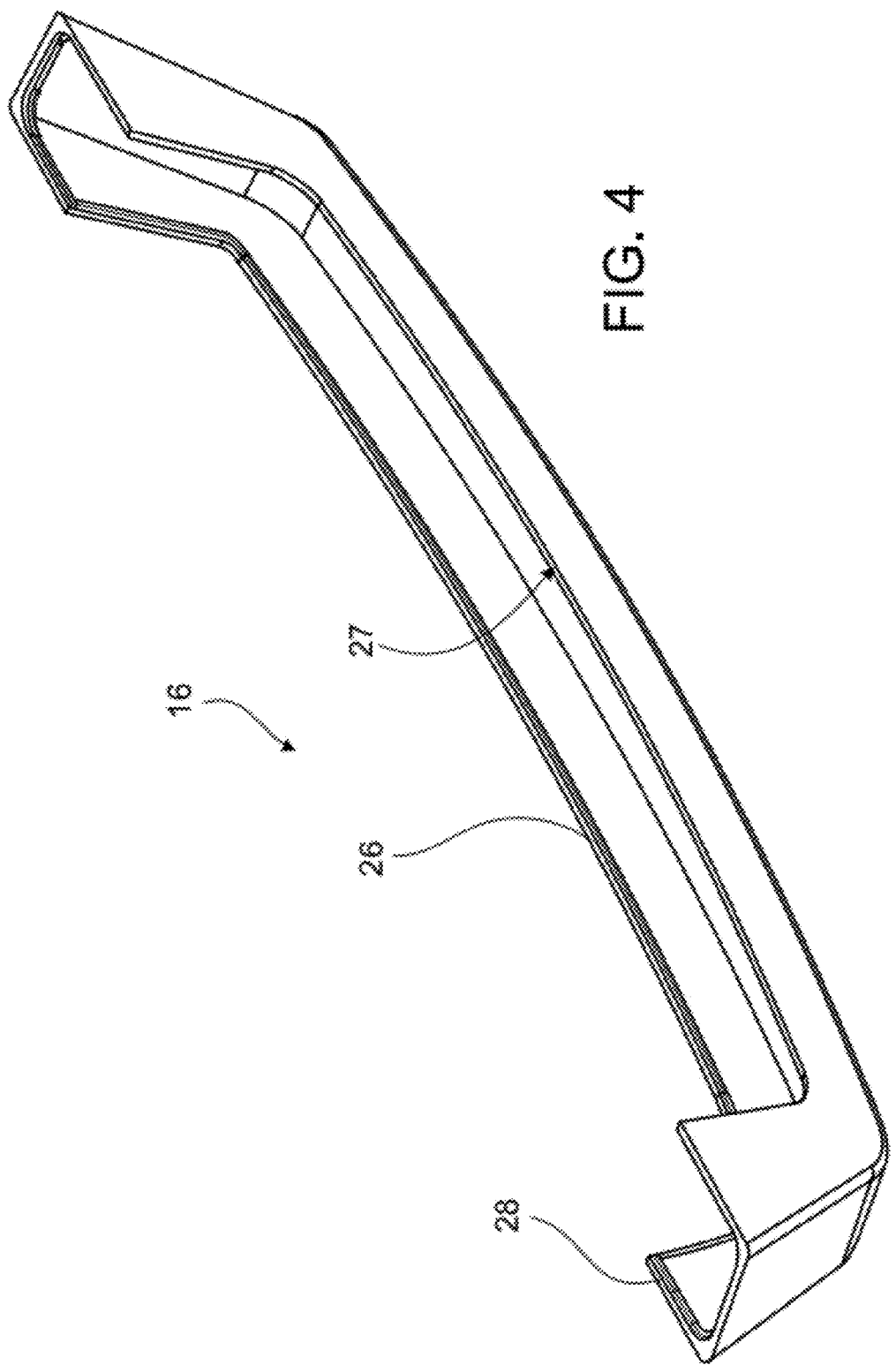
FIG. 4 is an isometric view of an outer part of the lamp body handle.

FIG. 4 shows an isometric view of the outer part 16 of the handle 6. The outer part 16 has a shape such that it precisely mates with the inner part 15 and is also ergonomically formed. The circumferential edges to which the counterparts 26, 27, 28 of the clips connections 23, 24, 25 are arranged are aligned with the related upper and lower edges of the inner part 15 and the fixing faces 22 in order to provide a gap that is as narrow and constant as possible for fulfilling hygienic requirements. The outer part 16 is made of the same translucent plastic material as the inner part 15 via injection molding.

Therefore, all faces which are visible from the outside constitute the second light emitting faces.

Other embodiments are within the scope of the following claims.

What is claimed is:

1. A surgical lamp, comprising:
    a carrying system;
    a lamp body configured to emit light;
    at least one handle connected to an outer circumference of the lamp body; and
    at least one illuminant disposed in the at least one handle, wherein at least a portion of the handle is made from a translucent material or has a translucent surface.

2. The surgical lamp of claim 1, wherein the translucent surface of the handle is a structured surface such that light emitted by the at least one illuminant is diffusely emitted through the translucent surface.

3. A surgical lamp, comprising:
    a carrying system;
    a lamp body configured to emit light;
    at least one handle connected to the lamp body; and
    at least one illuminant disposed in the at least one handle, wherein at least a portion of the handle has a translucent surface that is configured to allow light to pass therethrough in multiple different directions, and the translucent surface comprises at least first and second faces that abut one another.

4. A surgical lamp, comprising:
    a carrying system;
    a lamp body configured to emit light;
    at least one handle connected to the lamp body; and
    at least one illuminant disposed in the at least one handle, wherein the at least one handle comprises an outer part secured to an inner part and the outer part of the handle is made from a translucent material or has a translucent surface.

5. The surgical lamp of claim 1, 3, or 4, wherein the translucent surface has a curved shape.

6. The surgical lamp of claim 1 or 3, wherein the translucent surface covers substantially the entire handle.

7. The surgical lamp of claim 1, 3, or 4, wherein the handle is fixed to a surface of a housing of the lamp body.

8. The surgical lamp of claim 1, 3, or 4, wherein the translucent surface is configured so that the translucent surface does not modify a color of light that is emitted by the at least one illuminant.

9. The surgical lamp of claim 1, 3, or 4, wherein the translucent surface is configured to modify a color of light that is emitted by the at least one illuminant.

10. The surgical lamp of claim 1, 3, or 4, wherein the at least one illuminant is adapted to indicate a type of power supply being used to power the surgical lamp.

11. The surgical lamp of claim 1, 3, or 4, wherein the surgical lamp is configured so that the surgical lamp can be operatively connected to a conventional power supply and to an auxiliary power supply, and the at least one illuminant is connected in such a way that operation with the auxiliary power supply is indicated.

12. The surgical lamp of claim 11, wherein the emitted light comprises a different color when operating with the auxiliary power supply than when operating with the conventional power supply.

13. The surgical lamp of claim 1, 3, or 4, wherein the surgical lamp can be supplied by a conventional power supply and by an auxiliary power supply, and the handle comprises at least a second illuminant that indicates the operation with the auxiliary power supply.

14. The surgical lamp of claim 13, wherein light emitted by the second illuminant has a different color than light emitted by the at least one illuminant.

15. The surgical lamp of claim 1, 3, or 4, wherein a third illuminant is connected in such a way that a certain operating mode of the surgical lamp is indicated.

16. The surgical lamp of claim 1, 3, or 4, wherein a part of the translucent surface of the handle has a refractor-like construction.

17. The surgical lamp of claim 16, wherein light emitted through the part of the translucent surface having the refractor-like construction is emitted by at least a fourth illuminant.

18. The surgical lamp of claim 17, wherein the fourth illuminant is configured to emit light within a narrow-band wavelength.

19. A method, comprising:
    detecting a type of power supply being used to power the surgical lamp of claim 1, 3, or 4; and
    operating the illuminant of the surgical lamp to indicate the detected type of power supply to a user.

20. The method of claim 19, wherein the illuminant is operated in a manner to cause the illuminant to blink.

21. The method of claim 19, wherein the illuminant is operated to emit light of a first color if a first type of power supply is detected, and the illuminant is operated to emit light of a second color if a second type of power supply is detected.

22. The surgical lamp of claim 4, wherein the inner part of the handle is made from a translucent material or has a translucent surface.

23. The surgical lamp of claim 4, wherein the inner part of the handle is fastened to the lamp body.

24. A surgical lamp, comprising:
    a carrying system;
    a lamp body configured to emit light;
    at least one handle connected to an outer circumference of the lamp body, wherein at least a portion of the handle is made from a translucent material or has a translucent surface such that light can pass through the portion of the handle; and
    at least one illuminant facing the portion of the handle to emit light through the portion of the handle.

25. The surgical lamp of claim 24, wherein the at least one illuminant is disposed in the handle.

26. The surgical lamp of claim 24, wherein the translucent surface covers substantially the entire handle.

27. The surgical lamp of claim 24, wherein the handle is fixed to a surface of a housing of the lamp body.

28. A surgical lamp, comprising:
    a carrying system;
    a lamp body comprising a plurality of illuminants arranged to emit light and illuminate an operating field;
    at least one handle connected to the lamp body, wherein the at least one handle comprises an outer part secured to an inner part, and the outer part of the handle is made from a translucent material or has a translucent surface such that light can pass through the outer part of the handle; and
    at least one handle-lighting illuminant facing the outer part of the handle to emit light through the outer part of the handle.

29. The surgical lamp of claim 28, wherein the at least one handle-lighting illuminant is disposed in the handle.

30. The surgical lamp of claim 28, wherein the inner part of the handle is made from a translucent material or has a translucent surface.

31. The surgical lamp of claim 28, wherein the inner part of the handle is fastened to the lamp body.

32. The surgical lamp of claim 28, wherein the at least one handle-lighting illuminant is located outside of the lamp body.

* * * * *